(12) United States Patent
Yamanaka

(10) Patent No.: US 10,736,496 B2
(45) Date of Patent: Aug. 11, 2020

(54) MEDICAL WIRE AND MEDICAL EQUIPMENT

(71) Applicant: OLYMPUS CORPORATION, Tokyo (JP)

(72) Inventor: Noriaki Yamanaka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 145 days.

(21) Appl. No.: 15/953,672

(22) Filed: Apr. 16, 2018

(65) Prior Publication Data

US 2018/0235442 A1 Aug. 23, 2018

Related U.S. Application Data

(63) Continuation of application No. PCT/JP2015/081224, filed on Nov. 5, 2015.

(51) Int. Cl.
*A61B 1/005* (2006.01)
*B21C 37/04* (2006.01)
(Continued)

(52) U.S. Cl.
CPC .......... *A61B 1/0057* (2013.01); *A61B 1/0011* (2013.01); *B21C 37/045* (2013.01); *B21C 37/047* (2013.01); *A61B 17/29* (2013.01); *A61B 18/1445* (2013.01); *A61B 34/71* (2016.02); *A61B 90/30* (2016.02); *A61B 2017/00318* (2013.01); *A61B 2017/00327* (2013.01); *A61B 2017/2902* (2013.01); *A61B 2017/2905* (2013.01); *A61B 2018/1412* (2013.01); *A61M 25/0147* (2013.01); *A61M 2025/09191* (2013.01)

(58) Field of Classification Search
CPC ....... A61B 1/0057; A61B 34/70; A61B 34/71; A61B 2017/00318; A61B 2017/00323; A61M 25/0133–0147
See application file for complete search history.

(56) References Cited

U.S. PATENT DOCUMENTS

2012/0277526 A1 11/2012 Naito
2016/0325077 A1* 11/2016 Yamanaka ........... A61B 1/0011

FOREIGN PATENT DOCUMENTS

EP 2540211 A1 1/2013
EP 3100666 A1 12/2016
(Continued)

OTHER PUBLICATIONS

International Search Report dated Dec. 22, 2015 issued in PCT/JP2015/081224.

*Primary Examiner* — Eric D. Bertram
(74) *Attorney, Agent, or Firm* — Scully, Scott, Murphy & Presser, P.C.

(57) ABSTRACT

Provided is a medical wire including: a main wire-strand portion that is formed of a plurality of main wire strands and that extends over the entire length of the medical wire; and at least one sub wire-strand portion that is disposed at an outer circumference of the main wire-strand portion, that is secured to the main wire-strand portion, and that is formed of a sub wire strand, wherein the diameter of the sub wire strand is at least twice the diameter of the main wire strand, and a first region having a relatively small lateral cross-sectional area and a second region having a lateral cross-sectional area that is greater than that of the first region are included.

8 Claims, 17 Drawing Sheets

(51) Int. Cl.
*A61B 1/00* (2006.01)
*A61B 17/29* (2006.01)
*A61B 90/30* (2016.01)
*A61M 25/01* (2006.01)
*A61B 17/00* (2006.01)
*A61B 18/14* (2006.01)
*A61M 25/09* (2006.01)
*A61B 34/00* (2016.01)

(56) References Cited

FOREIGN PATENT DOCUMENTS

| | | |
|---|---|---|
| JP | H06-040619 Y2 | 10/1994 |
| JP | H07-279940 A | 10/1995 |
| JP | 2009-233225 A | 10/2009 |
| JP | 2012-157378 A | 8/2012 |
| JP | 5080702 B2 | 11/2012 |
| JP | 2015-139575 A | 8/2015 |
| WO | WO 2015/115196 A1 | 8/2015 |

* cited by examiner

MEDICAL WIRE AND MEDICAL EQUIPMENT

This is a continuation of International Application PCT/JP2015/081224, with an international filing date of Nov. 5, 2015, which is hereby incorporated by reference herein in its entirety.

TECHNICAL FIELD

The present invention relates to a medical wire and medical equipment.

BACKGROUND ART

There is a known medical wire that is provided with a main wire-strand portion provided over the entire length thereof in a longitudinal direction and a sub wire-strand portion that is secured to the main wire-strand portion at a portion of the main wire-strand portion in the longitudinal direction, and that has a first region having a relatively small lateral cross-sectional area and a second region having a lateral cross-sectional area that is greater than that of the first region (for example, see Patent Literature 1).

Because the medical wire of Patent Literature 1 is not a wire in which two types of wires having different rigidities are arranged next to each other in a longitudinal direction and are joined by means of welding or the like, there is no stress concentration at join sites, and thus, it is possible to prevent deterioration of the strength at the join sites, and the medical wire exhibits excellent performance in that it is possible, even in medical equipment provided with a flexible inserted portion, to suitably generate a desired driving force on the distal-end side thereof.

CITATION LIST

Patent Literature

{PTL 1} Japanese Unexamined Patent Application, Publication No. 2015-139575

SUMMARY OF INVENTION

An aspect of the present invention is a medical wire including: a main wire-strand portion that is formed of a plurality of main wire strands and that extends over the entire length of the medical wire; and at least one sub wire-strand portion that is disposed at an outer circumference of the main wire-strand portion, that is secured to the main wire-strand portion, and that is formed of at least one sub wire strand, wherein a diameter of the sub wire strand is at least twice a diameter of the main wire strand, and a first region having a relatively small lateral cross-sectional area and a second region having a lateral cross-sectional area that is greater than that of the first region are included.

Another aspect of the present invention is medical equipment including: an elongated inserted portion possessing flexibility; a treating portion that is provided at a distal-end portion of the inserted portion and that includes an end effector; a manipulating portion that is provided on a base-end side of the inserted portion and that serves for manipulating the treating portion; and a medical wire according to any one of Claims 1 to 8, wherein the first region is connected to the treating portion, and the second region is connected to the manipulating portion.

Advantageous Effects of Invention

The present invention affords an advantage in that it is possible, even in medical equipment provided with a flexible inserted portion, to generate a desired driving force on the distal-end side thereof with high responsiveness.

DESCRIPTION OF EMBODIMENT

A medical wire 1 according to an embodiment of the present invention will be described below with reference to the drawings.

Figure 1:
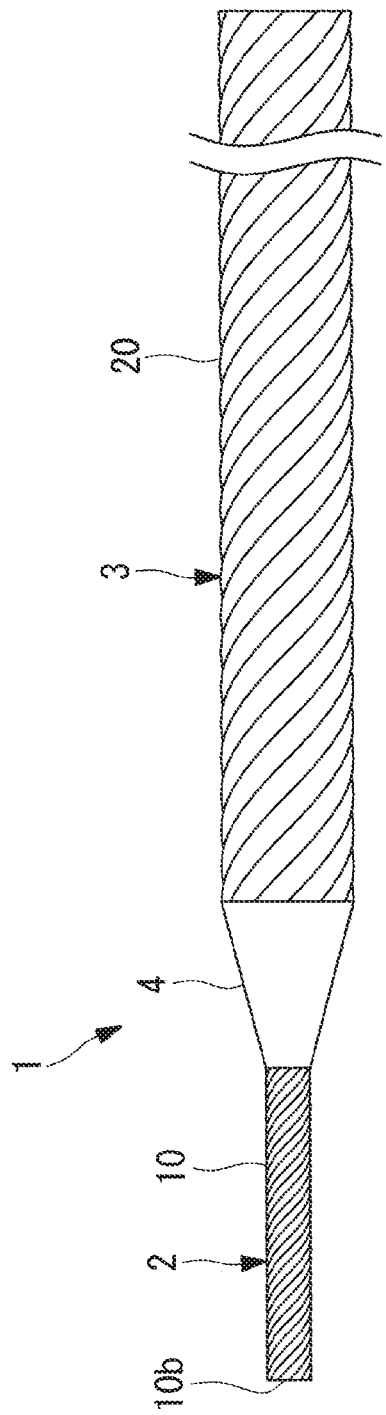
FIG. 1 is a side view showing a medical wire according to an embodiment of the present invention.

As shown in FIG. 1, the medical wire 1 according to this embodiment is provided with a main wire-strand portion 10 that is disposed over the entire length thereof in a longitudinal direction, and sub wire-strand portions 20 that are attached to a portion of the main wire-strand portion 10 in the longitudinal direction thereof.

Figure 2:
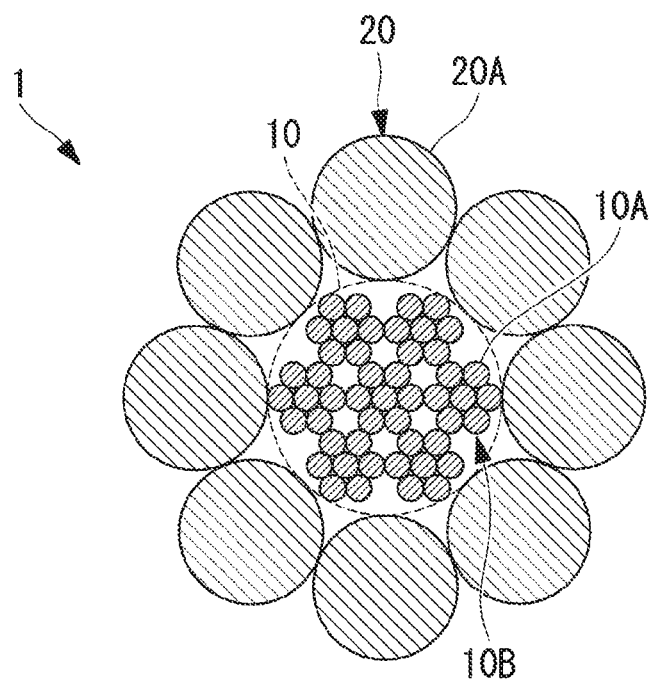
FIG. 2 is a lateral cross-sectional view of a second region of the medical wire in FIG. 1.

As shown in FIG. 2, the main wire-strand portion 10 is formed of one or more stranded wires 10B in which a plurality of main wire strands 10A are stranded. In the example shown in FIG. 2, the main wire-strand portion 10 is formed of seven stranded wires 10B in which seven main wire strands 10A are stranded.

The sub wire-strand portions 20 are provided so as to cover an outer circumferential surface of the main wire-strand portion 10 over a predetermined length from one end portion 10a of the main wire-strand portion 10. In the following, the one end portion 10a will be referred to as the base-end portion 10a, and an end portion 10b on the opposite side at which the sub wire-strand portions 20 are not provided will be referred to as the distal-end portion 10b.

In the example shown in FIG. 2, each of the sub wire-strand portions 20 is a single wire strand formed of a single sub wire strand 20A, the plurality of sub wire-strand portions 20 are arranged next to each other in a circumferential direction of the main wire-strand portion 10 and are stranded at the periphery of the main wire-strand portion 10. Such a configuration is achieved, for example, by removing, over a certain length, the individual sub wire-strand portions 20 of a wire formed around the main wire-strand portion 10 by stranding the sub wire-strand portions (strands) 20 formed of the plurality of single wire strands.

Figure 3:
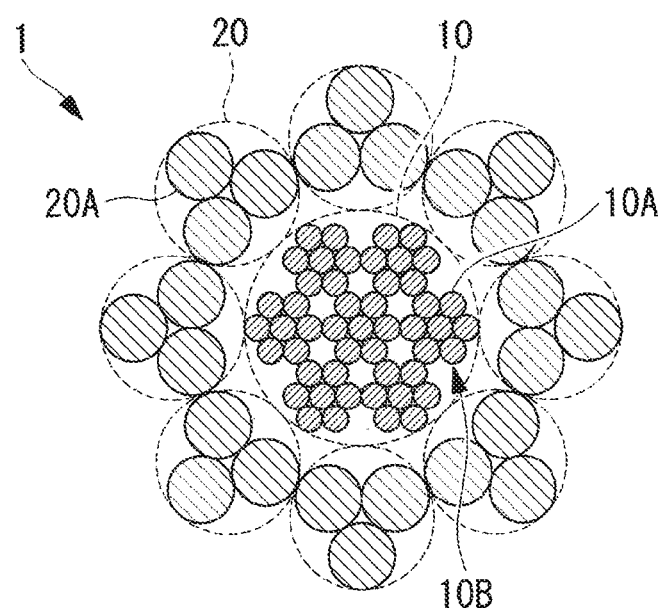
FIG. 3 is a lateral cross-sectional view of a second region of a modification of the medical wire in FIG. 1.
Figure 4:
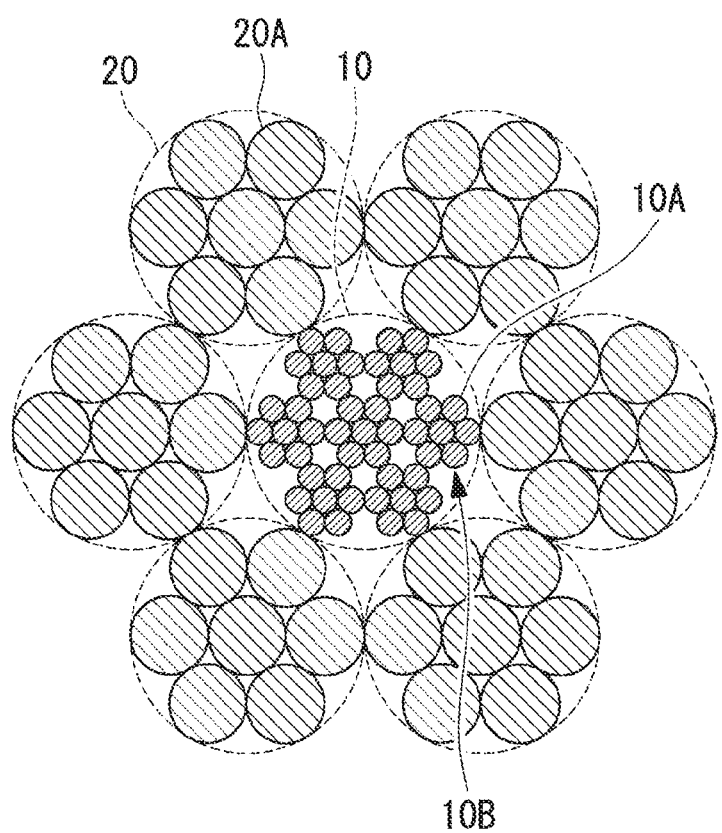
FIG. 4 is a lateral cross-sectional view of a second region of another modification of the medical wire in FIG. 1.

The main wire-strand portion 10 and the sub wire-strand portions 20 are both formed of, for example, a metal such as stainless steel or the like. The sub wire-strand portions 20 may be single wire strands, as shown in FIG. 2, or stranded wires formed by stranding the plurality of sub wire strands 20A, as shown in FIGS. 3 and 4. In the following, the case of the single wire strands shown in FIG. 2 will be described as an example.

All of the sub wire-strand portions 20 are joined with the main wire-strand portion 10 by means of soldering, brazing, laser welding, or the like, and are secured thereto so as not to move in longitudinal directions relative to the main wire-strand portion 10. Although it suffices that the sub wire-strand portions 20 are joined to the main wire-strand portion 10 at least at the boundary between a first region 2 and a second region 3, described later, the sub wire-strand portions 20 may be joined over their own lengths in the longitudinal direction.

In the medical wire 1, the second region 3 in which the sub wire-strand portions 20 are provided has a greater cross-sectional area in a radial direction (lateral cross-sectional area) than that of the first region 2 in which only the main wire-strand portion 10 is present. In other words, the medical wire 1 is provided with the first region 2 that is on the distal-end side and that has a relatively small lateral cross-sectional area and the second region 3 that is on the base-end side and that has a relatively larger lateral cross-sectional area.

In the second region 3, because the main wire-strand portion 10 and the plurality of sub wire-strand portions 20 are secured so as not to move relative to each other in the longitudinal directions, these components are integrally moved.

At the boundary between the first region 2 and the second region 3, a tapered portion 4 is provided by means of soldering, brazing, laser welding, or the like, and the radial size thereof is gradually and smoothly decreased from the second region 3 toward the first region 2.

In this embodiment, the diameter of the sub wire strand 20A is at least twice the diameter of the main wire strand 10A.

In addition, the diameter of the sub wire-strand portion (the same as the sub wire strand 20A in this embodiment) 20 is at most 1.5-times the diameter of the main wire-strand portion 10.

Therefore, the following conditional expression is satisfied in this embodiment.

$$2a < \frac{\sin\frac{\pi}{n}}{1-\sin\frac{\pi}{n}} \leq 1.5 \quad \{\text{Eq. 1}\}$$

where n is the number of the sub wire-strand portions 20, $d_c$ is the diameter of the main wire strand 10A, $D_c$ is the diameter of the main wire-strand portion 10, and a is $d_c/D_c$.

The upper limit of Eq. 1 is determined on the basis of the condition that the diameters of the sub wire-strand portions 20 are at most 1.5-times the diameter of the main wire-strand portion 10, and the lower limit of Eq. 1 is determined by means of the following computational expression.

In other words, assuming that the radius of the sub wire strand 20A is $r_m$, and the radius of the main wire-strand portion 10 is $R_c$, the following expression holds:

$$\sin(\pi/n) = r_m/(R_c + r_m).$$

Modifying the above expression gives:

$$r_m/R_c = \sin(\pi/n)/(1 - \sin(\pi/n)).$$

In addition, on the basis of the condition that the diameter of the sub wire strand 20A is at least twice the diameter of the main wire strand 10A, the following expression holds:

$$r_m \geq d_c = a \times D_c = 2aR_c;$$

and therefore, the following relationship holds:

$$2a \leq r_m/R_c.$$

The operation of the thus-configured medical wire 1 according to this embodiment will be described below.

With the medical wire 1 according to this embodiment, because the second region 3 on the base-end side has a greater lateral cross-sectional area than that of the first region 2 on the distal-end side, by appropriately setting the lateral cross-sectional area of the second region 3, it is possible to apply, to the base-end side, a force that is greater than the breaking tensile force of the main wire-strand portion 10.

In addition, because the diameters of the sub wire strands 20A of the sub wire-strand portions 20 are set to be at least twice the diameters of the main wire strands 10A of the main wire-strand portion 10, the flexural rigidities of the sub wire strands 20A are at least 16-times the flexural rigidities of the main wire strands 10A. As a result, the flexibilities of the sub wire strands 20A are decreased, and it becomes less likely for the sub wire-strand portions 20 to be stretched. Furthermore, because gaps between the main wire strands 10A and the sub wire strands 20A or gaps among the sub wire strands 20A are decreased, the influence of stretching due to the gaps is suppressed. As an effect thereof, there is an advantage in that it is possible to suppress initial stretching in which the medical wire 1 stretches when a tensile force is applied thereto from a state in which the tensile force is zero.

In addition, because the diameters of the sub wire-strand portions 20 are set to be at most 1.5-times the diameter of the main wire-strand portion 10, it is possible to set the outer diameter of the second region 3 to be at most four-times the outer diameter of the first region 2. As a result, it is possible to provide the medical wire 1 that has a sufficiently small diameter even in the second region 3 and that is suitable to be employed for driving a treatment tool or the like to be made to pass through a long, thin inserted portion.

Specifically, in the medical wire 1 according to this embodiment, assuming that the main wire-strand portion 10 is a stranded wire having at least 1×3 stranded wires and at most 7×7 stranded wires, the following relationship holds: 0.11≤a≤0.46.

In other words, for example, in the case in which the main wire-strand portion 10 is a stranded wire having 1×3 stranded wires, the following relationship holds between the diameter $D_c$ of the main wire-strand portion 10 and the radius $r_c$ of the main wire strand 10A:

$$D_c = 2 \times (1 + (2/\sqrt{3})) \times r_C,$$

thus resulting in $a = d_c/D_c = 0.46$.

In addition, for example, in the case in which the main wire-strand portion 10 is a stranded wire having 7×7 stranded wires, the following relationship holds between the diameter $D_c$ of the main wire-strand portion 10 and the radius $r_c$ of the main wire strand 10A:

$$D_c = 9 \times d_c,$$

thus resulting in $a = d_c/D_c = 0.11$.

Figure 5:
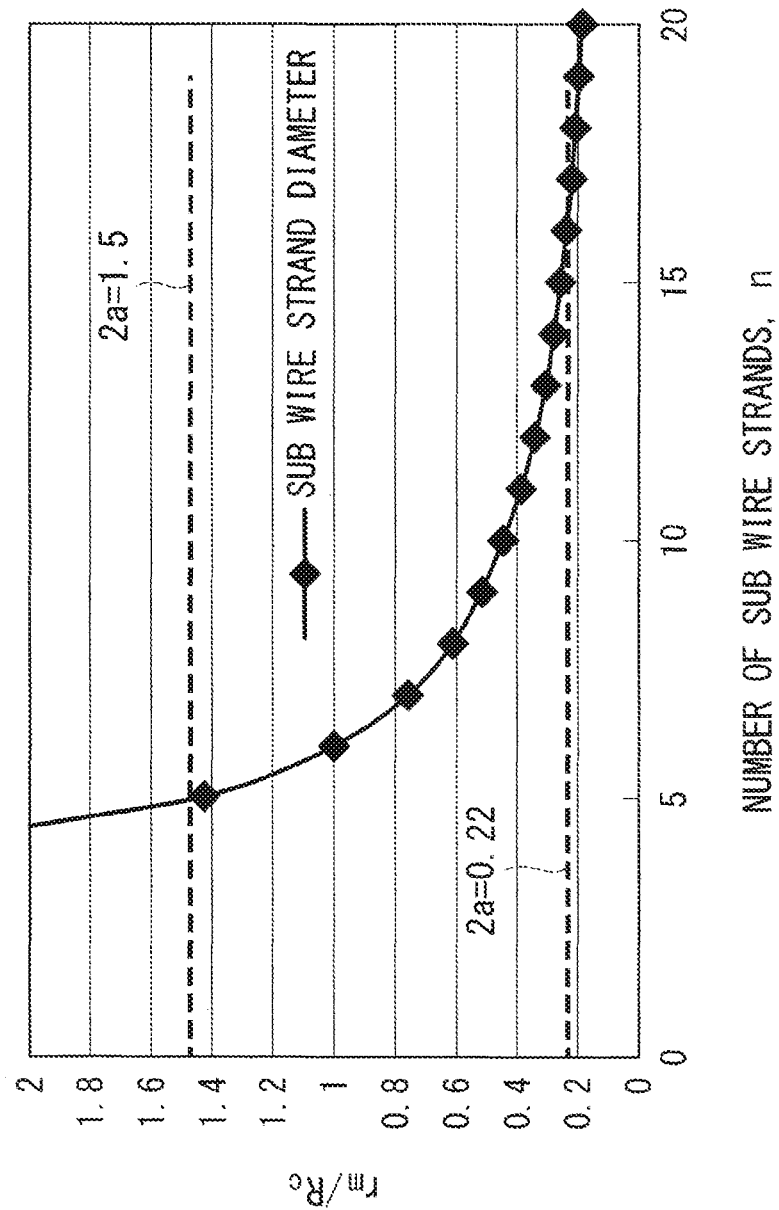
FIG. 5 is a diagram showing the relationship between the number of sub wire strands and the ratio of the diameter of a main wire strand and the diameter of the sub wire strand in the medical wire in FIG. 1.

Because the relationship between the number n of the sub wire strands 20A of the sub wire-strand portions 20 and the ratio $r_m/R_c$ of the radius $R_c$ of the main wire-strand portion 10 and the radius $r_m$ of the sub wire strand 20A is the relationship shown in FIG. 5, the number n of the sub wire strands 20A that satisfies Eq. 2 is as follows:

$$5 \leq n \leq 17.$$

Figure 6:
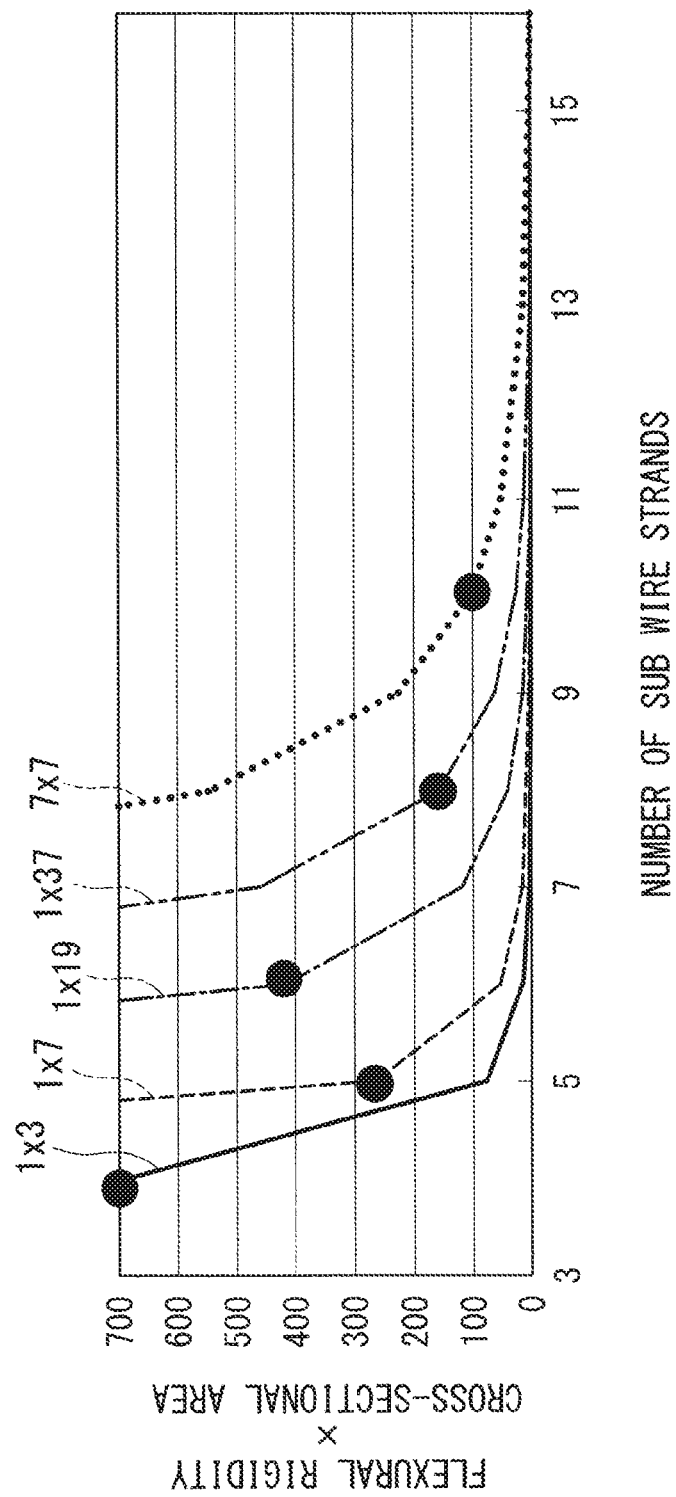
FIG. 6 is a diagram showing the relationship between the value of [flexural rigidity]×[lateral cross-sectional area] and the number of sub wire strands in the medical wire in FIG. 1.

Note that, in this embodiment, the diameters of the sub wire strands 20A are assumed to be at least twice the diameters of the main wire strands 10A; however, in the case in which the diameters of the sub wire strands 20A are set to be four-times the diameters of the main wire strands 10A, it is clear, as shown in FIG. 6, that the values of [flexural rigidity]×[lateral cross-sectional area] for the sub wire strands 20A are at least 100-times those for the main wire strands 10A in all cases in which the main wire-strand portion 10 is configured to be a stranded wire having at least 1×3 stranded wires and at most 7×7 stranded wires (filled plot in the figure).

In this case, it is possible to rewrite Eq. 1 as Eq. 2 below:

$$4a < \frac{\sin\frac{\pi}{n}}{1 - \sin\frac{\pi}{n}} \leq 1.5 \quad \{\text{Eq. 2}\}$$

In addition, in this case, the number n of the sub wire strands 20A is as follows:

$$5 \leq n \leq 10.$$

By doing so, because the initial-stretching characteristics of the medical wire 1 are determined by the sub wire-strand portions 20, there is an advantage in that it is possible to easily realize flexibility of the main wire-strand portion 10 and a reduction of initial stretching in the entire medical wire 1.

In addition, in this embodiment, although the main wire strands 10A and the sub wire strands 20A are formed of the same material, alternatively, the sub wire strands 20A may be formed of a material having a greater Young's modulus than that of the main wire strands 10A.

By setting the rigidities of the sub wire-strand portions 20, which greatly affect initial stretching, to be greater than that of the main wire-strand portion 10, it is possible to even more effectively decrease the initial stretching.

In addition, because the rigidity of the second region 3 is increased due to an increase in the cross-sectional area thereof in the radial direction, the second region 3 is less likely to be stretched in the longitudinal direction as compared to the first region 2. The attenuation of the force on the distal-end side is caused by friction, and, although the medical wire 1 is stretched in the longitudinal direction due to this friction, it is possible, by suppressing stretching of the medical wire 1, to reliably cause a large force to act on the distal-end portion relative to the amount by which the wire is manipulated.

In addition, in the medical wire 1, the main wire-strand portion 10 and the sub wire-strand portions 20 are in contact with each other along the longitudinal direction of the sub wire-strand portions 20. Because of this, it is possible to increase the contact area between the main wire-strand portion 10 and the sub wire-strand portions 20. As a result, a large frictional force is generated between the main wire-strand portion 10 and the sub wire-strand portions 20, and thus, it is possible to considerably decrease the occurrence of a situation in which the joint therebetween fails.

In addition, because the tapered portion 4 is provided at the boundary between the first region 2 and the second region 3, even in the case in which the medical wire 1 is made to pass through a buckling-prevention wire sheath (described later) or the like, the sub wire strands 20A near the boundary are less likely to get caught on the wire sheath or the like, and thus, it is possible to achieve suitable reciprocating driving.

In this embodiment, the tapered portion 4 is not an essential structure. Therefore, it is possible to employ a configuration in which the boundary between the first region 2 and the second region 3 has the greatest radial-direction size by joining the main wire-strand portion 10 and the plurality of sub wire-strand portions 20, for example, by means of swaging or the like.

Figure 7:
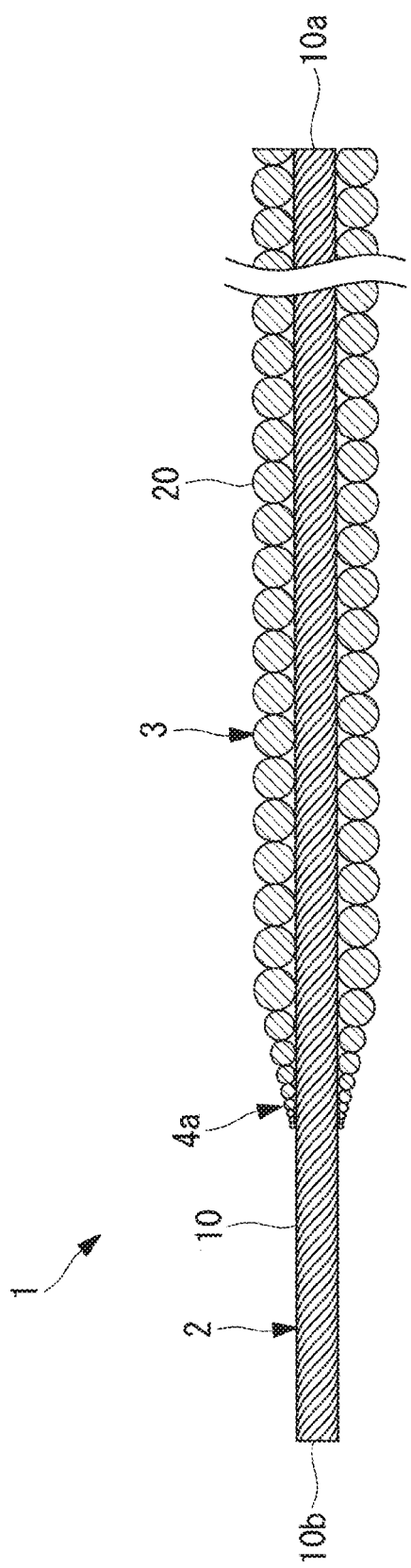
FIG. 7 is a longitudinal cross-sectional view showing a modification of a tapered portion of the medical wire in FIG. 1.
Figure 8:
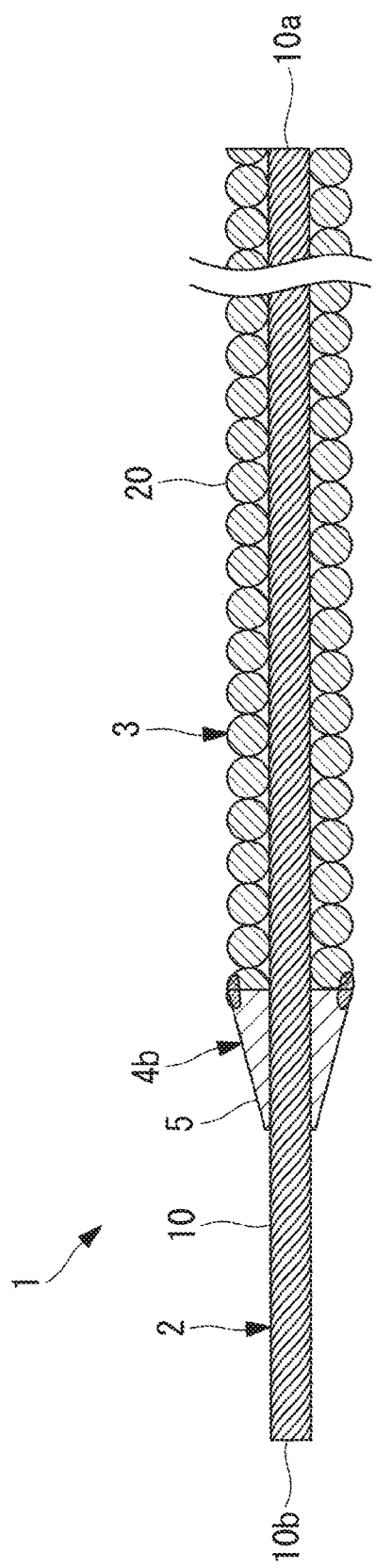
FIG. 8 is a longitudinal cross-sectional view showing another modification of the tapered portion of the medical wire in FIG. 1.

In addition, in the case in which the tapered portion 4 is formed, the method used for the formation thereof is not limited to the above-described method. For example, as in a modification thereof shown in FIG. 7, a tapered portion 4a may be formed by causing, by means of publically-known swaging or the like, the diameters of the plurality of sub wire-strand portions 20 themselves to gradually become smaller toward the distal ends thereof. In addition, as shown in FIG. 8, a substantially truncated-cone-shaped cover 5 may be placed over the distal-end portions of the sub wire-strand portions 20, and a tapered portion 4b may be formed by joining the cover 5 and the sub wire-strand portions 20 by means of soldering, brazing, laser welding, or the like.

Next, medical equipment 101 according to the embodiment of the present invention will be described.

Figure 9:
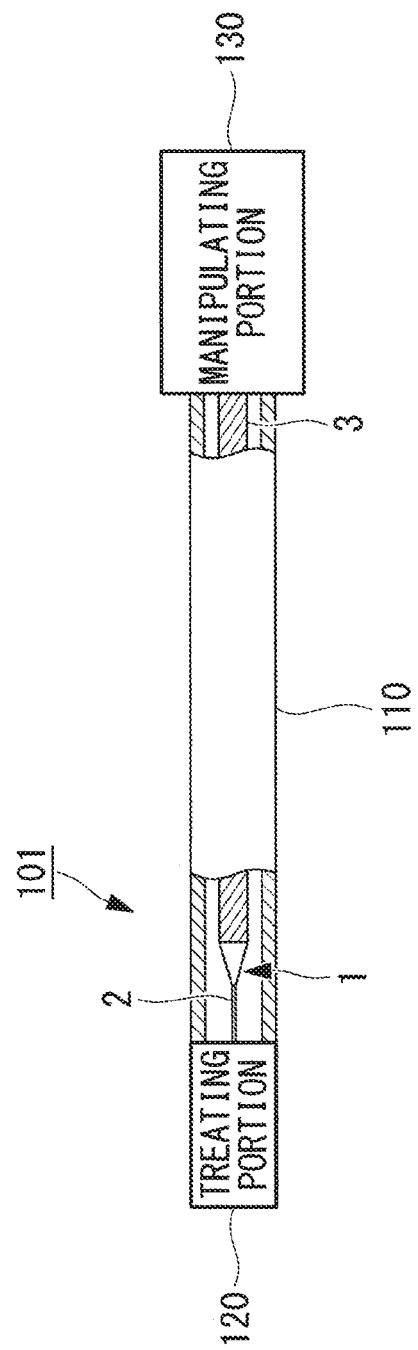
FIG. 9 is a schematic diagram showing a basic configuration of medical equipment to which the medical wire in FIG. 1 is applied.

As shown in FIG. 9, the medical equipment 101 according to this embodiment is provided with: an elongated inserted portion 110 possessing flexibility; a treating portion 120 that is provided at a distal-end portion of the inserted portion 110; a manipulating portion 130 that is provided at a base-end portion of the inserted portion 110; and the medical wire 1.

The inserted portion 110 has a publically-known configuration provided with a sheath formed of a resin, a coil, or the like, a coiled tube made of a metal, and so forth. As will be described later, in a portion of the inserted portion 110, a bending portion 160 that can be actively bent may be provided.

The treating portion 120 includes an end effector that is disposed at the distal-end portion of the medical equipment 101 and that executes a certain task. Examples of the end effector include various types of surgical tools, such as grasping forceps, an electrosurgical knife, and so forth, as well as an observation apparatus or the like, such as an image-acquisition unit provided with an image-acquisition device and an illumination unit.

The manipulating portion 130 is for driving the medical wire 1, which is made to pass through the inserted portion 110, in a reciprocating manner in the longitudinal direction of the inserted portion 110. The medical wire 1 may be manually driven by a surgeon or the like or electrically driven by means of a motor or the like. With the manipulating portion 130, it is possible to select and employ, as appropriate, various publically-known configurations employing one of manual drive and electrical drive.

The medical wire 1 is made to pass through the inserted portion 110. The first region 2 at the distal-end portion of the medical wire 1 is connected to the end effector, a member for driving the end effector, or the like in the treating portion 120. The second region 3 at the base-end portion of the medical wire 1 is connected to the manipulating portion 130. By doing so, it is possible to achieve a desired effect by driving the treating portion 120 by driving the medical wire 1 in a reciprocating manner via the manipulating portion 130.

From the viewpoint of achieving a satisfactory effect of the medical wire 1, it is preferable that, in the medical equipment 101, a tensile force applied to the second region 3 from the manipulating portion 103 be set to be equal to or greater than the breaking strength of the first region 2 and less than the breaking strength of the second region 3. By doing so, it is possible to apply a large force to the first region 2.

The magnitude of the force to be applied to the first region 2 can be set, as appropriate, within a range that is less than the breaking strength of the first region 2. The magnitude of the tensile force that needs to be applied to the second region 3 relative to the magnitude of the force to be applied to the first region 2 can be calculated. For example, a tensile force T that needs to be applied to the second region 3 can be calculated by using the following expression, assuming that the tensile force in the first region 2 is $T_o$, the coefficient of friction with respect to the member that comes into contact with the medical wire 1 is $\mu$, and the bending angle of the inserted portion 110 is $\theta$. Note that e means a base of natural logarithm in the following expression.

$$T=T_o e^{\mu\theta}$$

Regarding the manner in which the medical wire 1 is made to pass through the inserted portion 110 and the manner in which the first region 2 is connected to the end effector or the like, various forms are conceivable.

Figure 10:
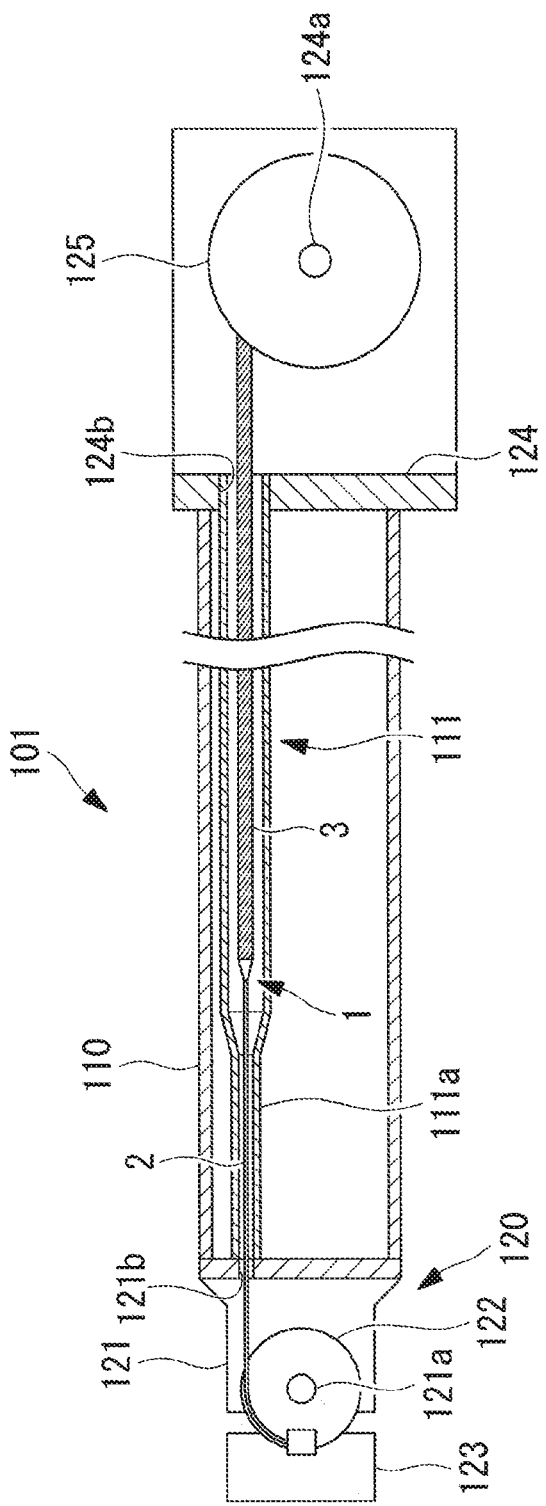
FIG. 10 is a diagram showing a first example of the form in which the medical wire is connected to the medical equipment in FIG. 9.

In the medical equipment 101 shown in FIG. 10, the treating portion 120 is provided with: a rigid support member 121 having a rotation shaft 121a; a pulley 122 that is supported by the rotation shaft 121a in a rotatable manner; and an end effector 123 attached to the pulley 122. In addition, the manipulating portion 130 is provided with: a support member 124 having a rotation shaft 124a; and a pulley 125 that is supported by the rotation shaft 124a in a rotatable manner.

The support member 121 is attached to a distal end of the inserted portion 110. An end portion of the first region 2 of the medical wire 1 is secured to the pulley 122. In addition, an end portion of the second region 3 of the medical wire 1 is secured to the pulley 125.

In this case, it is preferable that the treating portion 120 and the manipulating portion 130 satisfy the following conditional expression:

$$d_a/d_c < d_j/d_m,$$

where $d_a$ is the minimum bending radius of the first region 2 due to the pulley 122 of the treating portion 120; $d_j$ is the minimum bending radius of the second region 3 due to the pulley 125 of the manipulating portion 130; $d_c$ is the diameter of the main wire strand 10A; and $d_m$ is the diameter of the sub wire strand 20A.

By doing so, the minimum bending radii $d_a$ and $d_j$ are set in accordance with the diameters of the individual wire strands 10A and 20A, and thus, it is possible to prevent breakage of the medical wire 1 and changes in the characteristics thereof.

Here, although a case in which the treating portion 120 is provided with one pulley has been illustrated, in the case in which the medical wire 1 is made to pass through a plurality of pulleys, the minimum bending radius of the first region 2 refers to the minimum bending radius among bending radii of the above-described plurality of pulleys. In the manipulating portion 130 also, in the case in which the second region 3 is threaded through a plurality of pulleys, the minimum bending radius refers to the minimum bending radius among bending radii of the plurality of pulleys. In addition, in the manipulating portion 130, the second region 3 may be linearly driven at the end portion in a reciprocating manner.

The medical wire 1 is made to pass through a buckling-prevention wire sheath 111 that is made to pass through the inserted portion 110. A distal end of the wire sheath 111 is secured to the support members 121 and 124, and holes 121b and 124b formed in the support members 121 and 124 are communicated with an internal space in the wire sheath 111. On the distal-end side of the wire sheath 111, a small-diameter portion 111a having a smaller diameter than that on the base-end side is formed. The inner diameter of the small-diameter portion 111a is set to have a size that does not allow the second region 3 of the medical wire 1 to be moved thereinto.

With this medical equipment 101, it is possible to reduce the diameter of the wire sheath 111 on the distal-end side by means of the small-diameter portion 111a, and thus, it is possible to reduce the size of the support member 121. Furthermore, because it is not necessary to make the second region 3 pass through the treating portion 120, as shown in FIG. 10, it is also possible to reduce the sizes of the pulley 122 and the end effector 123, and to reduce the diameter of the treating portion 120 so as to be smaller than that of the inserted portion 110.

In the case of an endoscope treatment tool or the like in which the medical equipment 101 is inserted into a channel of an endoscope, the area of the field of view of the endoscope occupied by the treating portion 120 is decreased, and thus, it is possible to easily perform treatment while suitably checking tissue in the surrounding area. Although a wire has, depending on the diameter thereof, a limit to the minimum diameter of a pulley around which the wire can be threaded, with the medical wire 1, because the size of the first region 2 in the radial direction is decreased, it is possible to suitably cope with the size reduction of the pulley 122.

In addition, because it is possible to decrease the clearance between the first region 2 and an inner surface of the wire sheath 111 by providing the small-diameter portion 111a, the medical wire 1 is less likely to move (to be loose) in the radial direction inside the wire sheath 111. Therefore, it is possible to smoothly move the medical wire 1 in a reciprocating manner. In addition, by providing the small-diameter portion 111a, there is an advantage in that it is possible to enhance the flexibility of the region in which the small-diameter portion 111a is provided in the inserted portion 110.

In this example, because the medical wire 1 is prevented from being moved farther forward when the second region 3 comes into contact with the small-diameter portion 111a, the length of the first region 2 and the length of the small-diameter portion 111a may be set in consideration of the maximum amount by which the end effector 123 is driven (the maximum amount by which the pulley 122 is rotated). Alternatively, the second region 3 may be used as a stop by taking advantage of the fact that forward movement is prevented.

Figure 11:
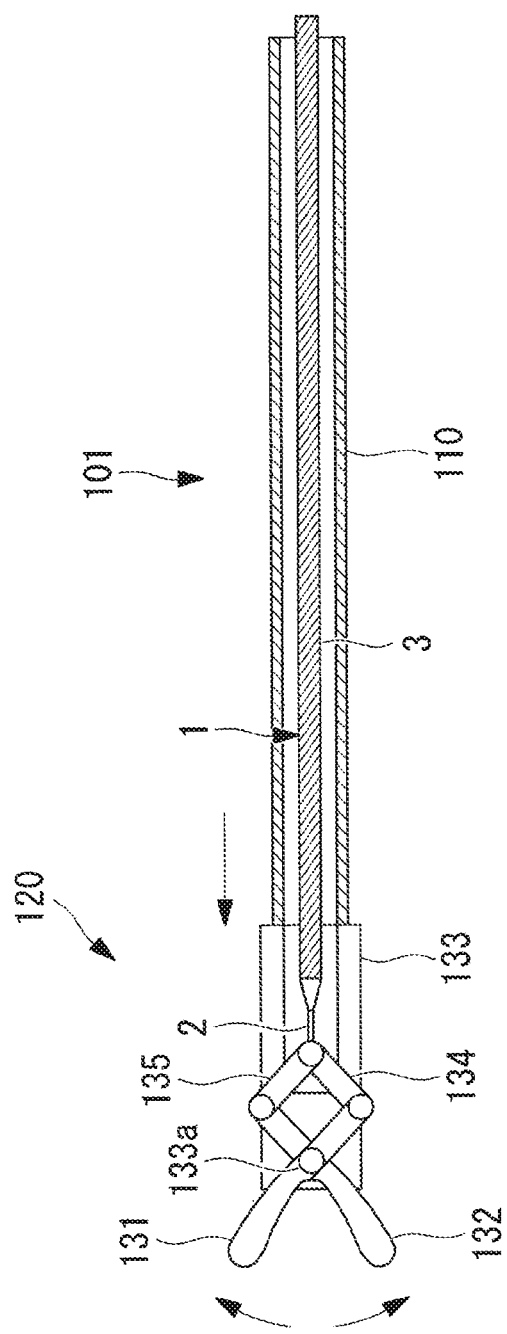
FIG. 11 is a diagram showing a second example of the form in which the medical wire is connected to the medical equipment in FIG. 9.
Figure 12:
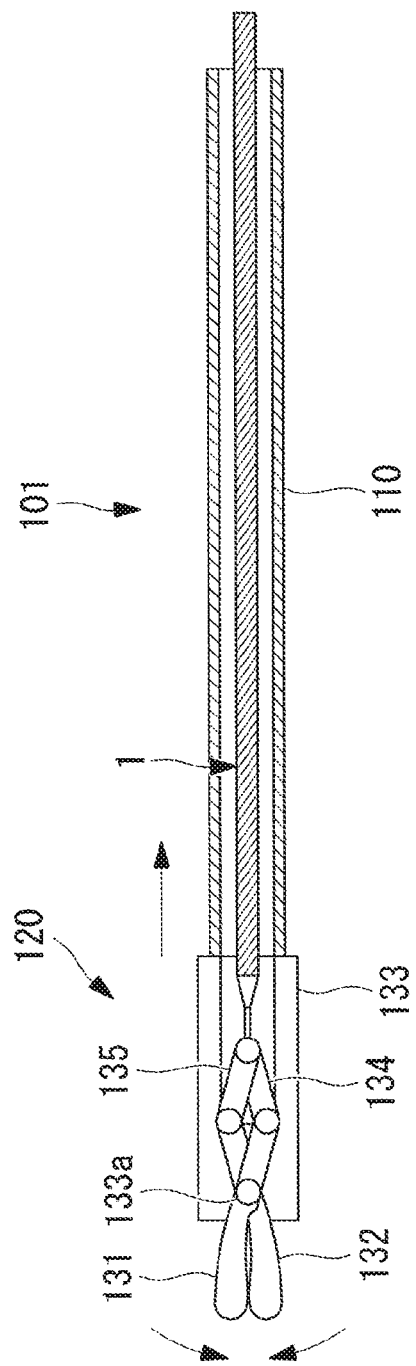
FIG. 12 is a diagram showing a third example of the form in which the medical wire is connected to the medical equipment in FIG. 9.

The medical equipment 101 shown in FIGS. 11 and 12 is an example in which the treating portion 120 is provided with a pair of forceps members 131 and 132 as an end effector. The medical wire 1 is not made to pass through a wire sheath but is made to directly pass through the inserted portion 110. The pair of forceps members 131 and 132 are supported, in a rotatable manner, by a rotation shaft 133a provided in a support member 133.

Base ends of the forceps members 131 and 132 are individually connected to linkage members 134 and 135, and base ends of the linkage members 134 and 135 are supported by the distal-end portion of the medical wire 1. By doing so, when the medical wire 1 is moved forward, the pair of forceps members 131 and 132 are opened, as shown in FIG. 11, and, when the medical wire 1 is moved backward, the pair of forceps members 131 and 132 are closed, as shown in FIG. 12.

In the case in which the wire is used as a transmitting member, although it is easy to transmit a force in a direction in which the wire is pulled, buckling or the like sometimes occurs in the case of manipulation in a direction in which the wire is pushed in, thus making it difficult to suitably transmit the amount of force involved in the manipulation. In particular, with the medical wire 1, because the size of the first region 2 in the radial direction is decreased, buckling is more likely to occur therein than it does in the second region 3.

The above-described points are taken into consideration in this example, and, as shown in FIG. 12, the boundary between the first region 2 and the second region 3 is set so as to be in the rigid support member 133 even when the medical wire 1 is maximally moved back. By doing so, because the first region 2 is always positioned in the support member 133, the first region 2 is not affected by bending of the inserted portion 110, and thus, it is possible to suitably suppress the occurrence of buckling or the like.

Figure 13:
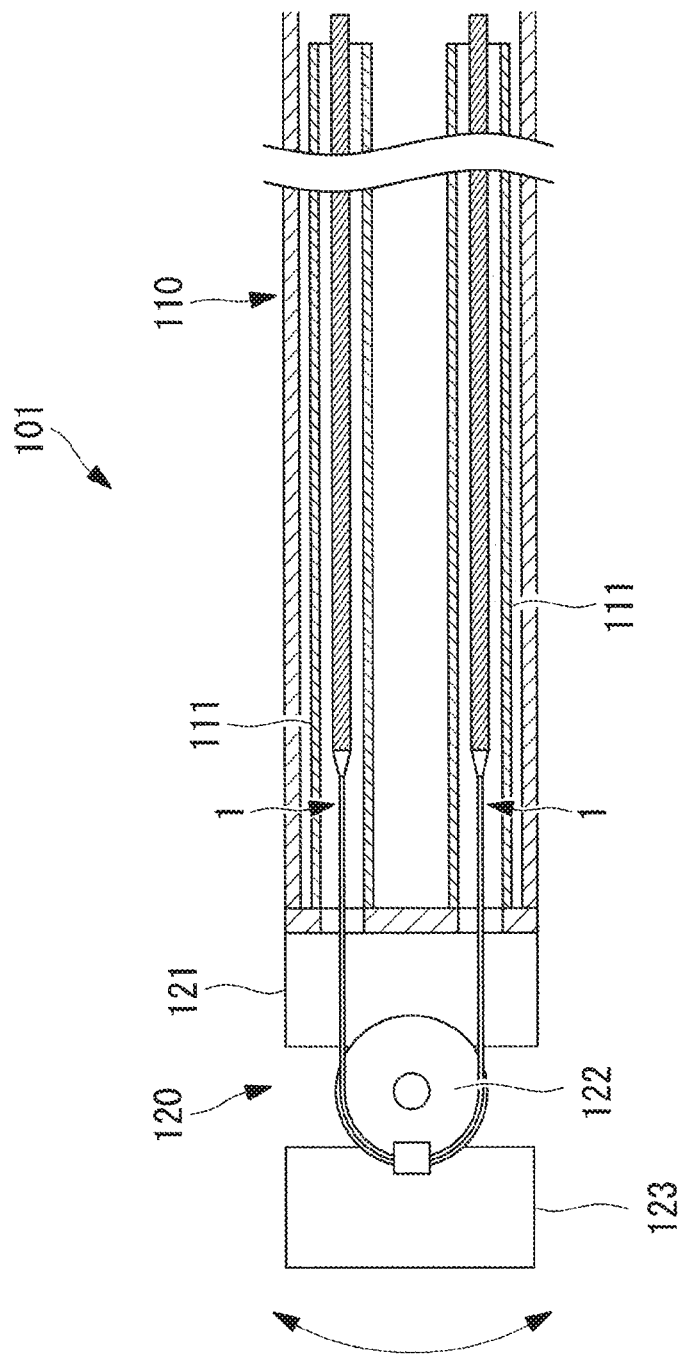
FIG. 13 is a diagram showing a fourth example of the form in which the medical wire is connected to the medical equipment in FIG. 9.

With the medical equipment 101 shown in FIG. 13, two medical wires 1 are employed. Distal-end portions of the individual medical wires 1 are secured to the same pulley 122, and thus, by pulling one of the medical wires 1, the pulley 122 can be rotated in one direction, and, by pulling the other medical wire 1, the pulley 122 can be rotated in the other direction. A structure in which, when one of the medical wires 1 is being pulled, the other medical wire 1 is pushed in may be employed, as needed.

In the case in which wires are employed as transmitting members in so-called antagonistic driving in which a pair of transmitting members are employed, it is known that there are cases in which slack occurs or transmission becomes insufficient due to stretching of the wires. However, when the medical wires 1 according to this embodiment are employed as transmitting members, it is possible to suitably drive even the treating portion 120, in which the size thereof is reduced by employing the first region 2 having a small size in the radial direction, while performing transmission by means of the second region 3, which is less likely to be stretched.

Figure 14:
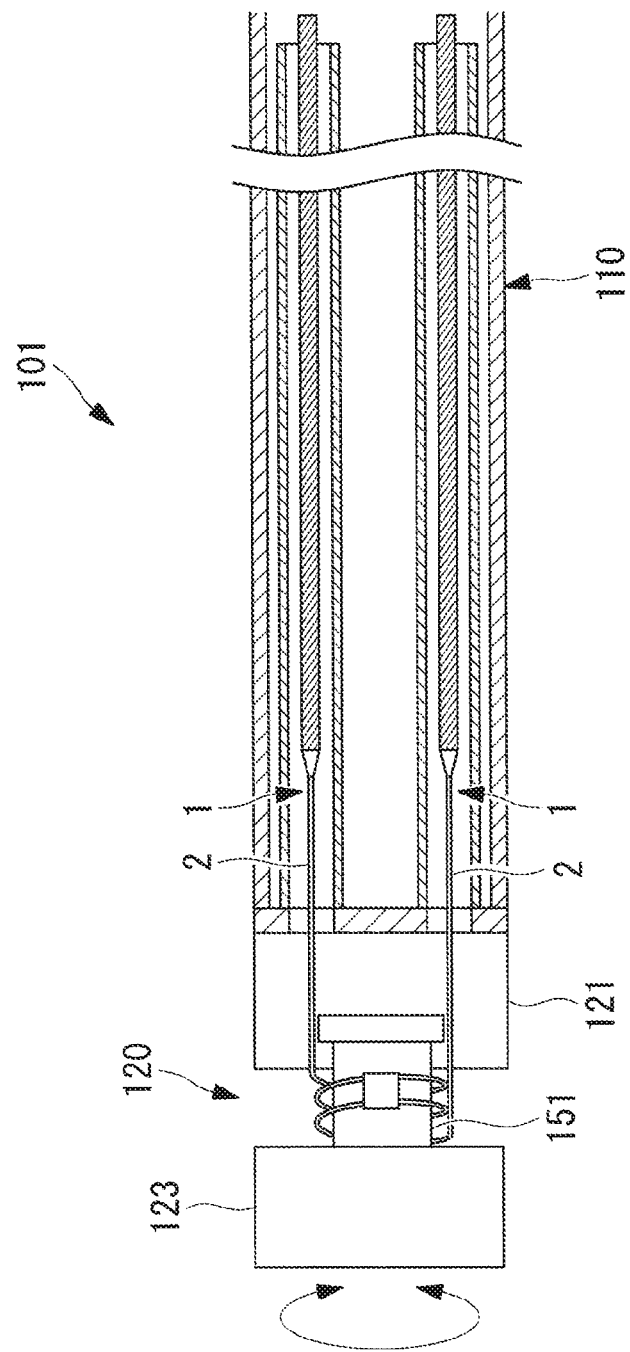
FIG. 14 is a longitudinal cross-sectional view showing another example of a treating portion in the medical equipment in FIG. 13.

As the treating portion 120 driven by using the pair of medical wires 1, various forms other than that shown in FIG. 13 are conceivable. With the medical equipment 101 shown in FIG. 14, a pulley 151 is attached to the treating portion 120 so as to be rotated about the axis of the inserted portion 110, and the first regions 2 of the pair of medical wires 1 are secured to the pulley 151 by being threaded therearound. By pushing and pulling the pair of medical wires 1, it is possible to rotationally drive the end effector 123 attached to the pulley 151 about the axis of the inserted portion 110.

Figure 15:
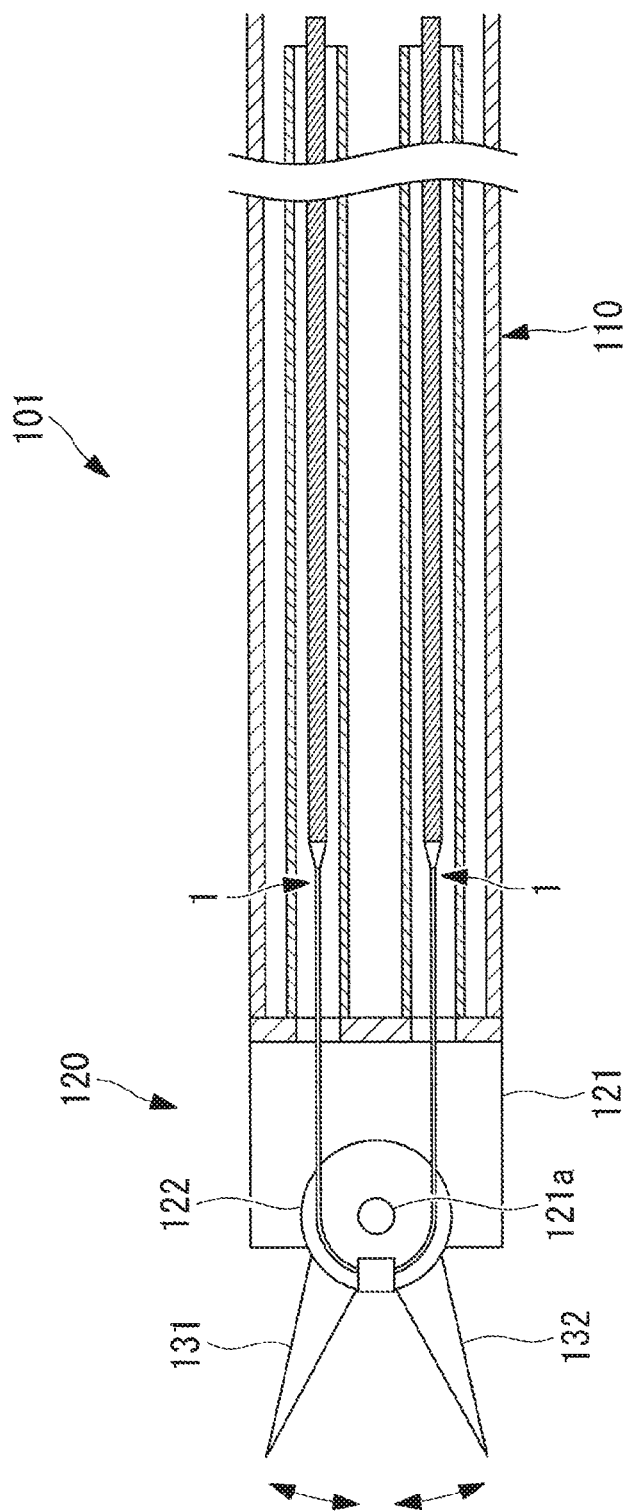
FIG. 15 is a longitudinal cross-sectional view showing another example of the treating portion in the medical equipment in FIG. 13.

With the medical equipment 101 shown in FIG. 15, one of the pair of forceps members 131 and 132 is attached to the pulley 122 in the treating portion 120. A second pulley (not shown) is attached to the back side of the pulley 122 coaxially with the pulley 122, and another pair of medical wires 1 are secured to the second pulley in a similar manner. The other one of the pair of forceps members 131 and 132 is attached to the second pulley. In this example, by driving the pulley 122 and the second pulley in a coordinated manner by manipulating the two pairs of medical wires 1, it is possible to open and close the pair of forceps members 131 and 132 and to change the orientation of the forceps members 131 and 132 in the closed state.

Figure 16:
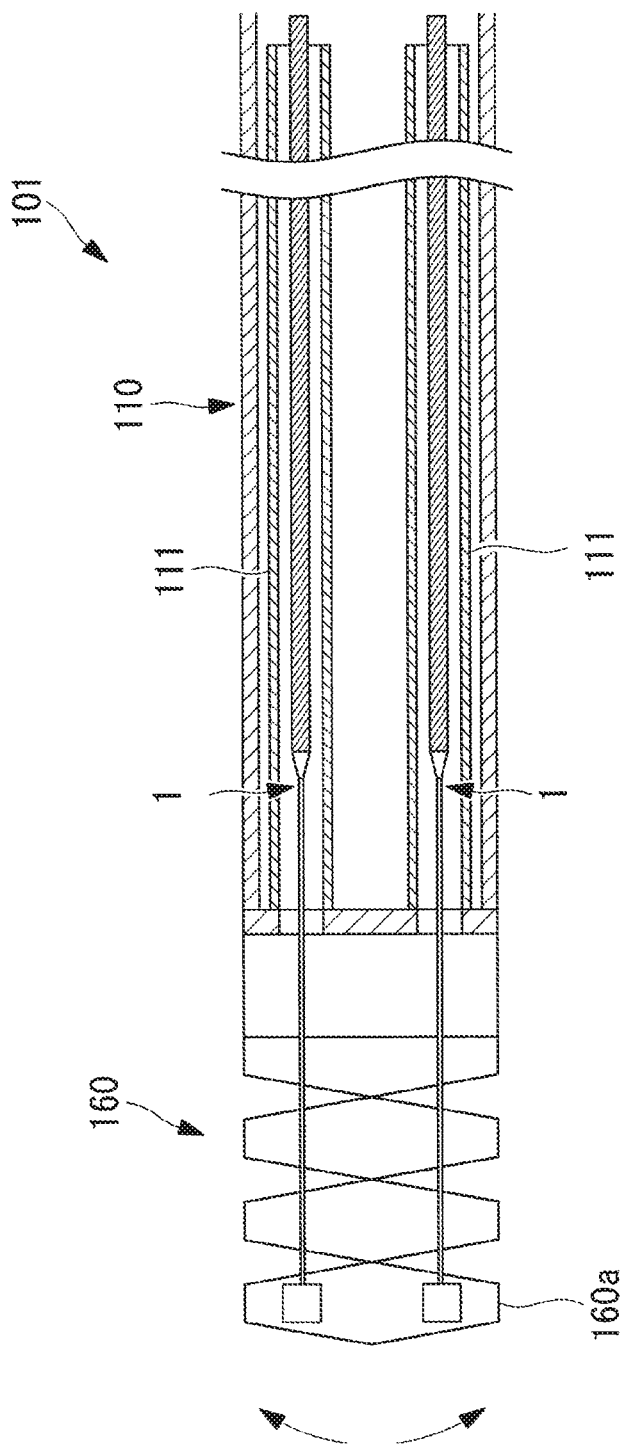
FIG. 16 is a longitudinal cross-sectional view showing an example in which the medical wire is connected to a bending portion in the medical equipment in FIG. 13.

The objects to be driven by the medical wires 1 are not limited to the treating portion 120. In FIG. 16, the pair of medical wires 1 are connected to a bending portion 160 for bending the inserted portion 110. The bending portion 160 has a publically-known structure in which a plurality of joint rings or bending pieces (hereinafter, referred to as "joint rings or the like") are disposed by being arrayed in the axial direction of the inserted portion 110, and, by pushing and pulling the pair of medical wires 1 that are connected to joint rings or the like 160a on the most distal-end side, it is possible to bend the inserted portion 110 in two directions.

Figure 17:
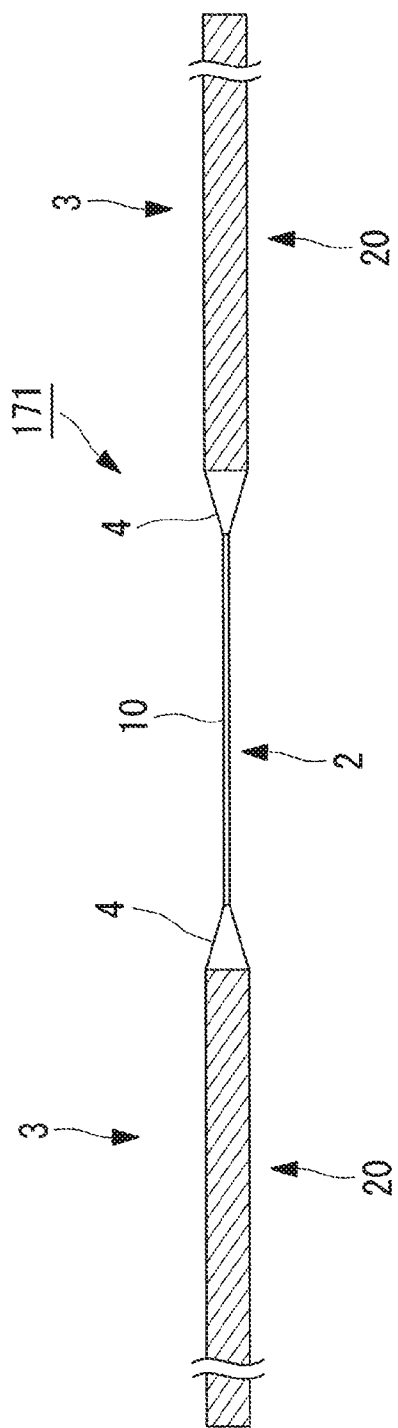
FIG. 17 is a diagram showing a modification of the medical wire used in the medical equipment in FIG. 12.

In addition, as shown in FIG. 17, a medical wire 171 having the second regions 3 at both end portions thereof in the longitudinal direction may be employed instead of the pair of medical wires 1. However, in the case in which a hole is provided in a support member 172 and the first region 2 is made to pass therethrough, it is not possible to make the medical wire 171 pass through the hole unless the inner diameter of the hole is set to have a value that is equal to or greater than the outer diameters of the second regions 3.

Figure 18:
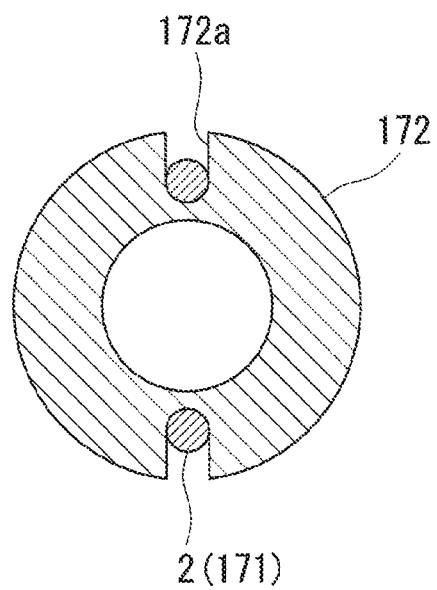
FIG. 18 is a lateral cross-sectional view showing a support member used when employing the medical wire in FIG. 17.
Figure 19:
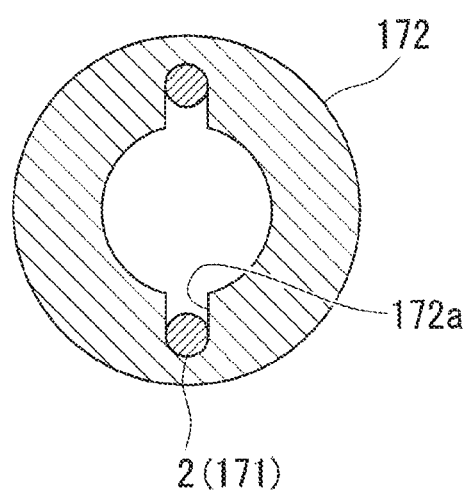
FIG. 19 is a lateral cross-sectional view showing another example of the support member used when employing the medical wire in FIG. 17.

In this case, as shown in FIG. 18, by providing the support member 172 with a groove 172a having a width in accordance with the outer diameter of the first region 2, it is possible to dispose the first region 2 in the treating portion 120. Because it is not necessary to make the second region 3 pass through the groove 172a, the width of the groove 172a may be set in accordance with the diameter of the first region 2. As shown in FIG. 18, such a groove 172a may be provided in an outer circumferential surface of the support member 172. In addition, as shown in FIG. 19, a groove 172b may be provided in an inner circumferential surface of the support member 172.

The medical wire 1 of the present invention may be employed as a transmitting member for driving an arm or the like provided in a distal-end portion of a treatment endoscope apparatus (not shown), or as a transmitting member for driving a treatment tool that is used by being made to pass through a channel of the treatment endoscope apparatus.

Furthermore, in the above-described individual embodiments, although examples in which at least portions of the individual sub wire-strand portions 20 are joined with the main wire-strand portion 10, it is permissible not to provide the join sites so long as the sub wire-strand portions 20 and the main wire-strand portion 10 are satisfactorily secured such that relative movements therebetween are prevented due to frictional forces or the like generated between the sub wire-strand portions 20 and the main wire-strand portion 10. As a result, the above-described embodiment leads to the following aspects.

An aspect of the present invention is a medical wire including: a main wire-strand portion that is formed of a plurality of main wire strands and that extends over the entire length of the medical wire; and at least one sub wire-strand portion that is disposed at an outer circumference of the main wire-strand portion, that is secured to the main wire-strand portion, and that is formed of at least one sub wire strand, wherein a diameter of the sub wire strand is at least twice a diameter of the main wire strand, and a first region having a relatively small lateral cross-sectional area and a second region having a lateral cross-sectional area that is greater than that of the first region are included.

With this aspect, because the flexural rigidity is proportional to the fourth power of the diameter, by setting the diameter of the sub wire strand to be at least twice the diameter of the main wire strand, it is possible to set the flexural rigidity of the sub wire strand to be at least 16-times the flexural rigidity of the main wire strand in the case in which materials of the wire strands are the same. By doing so, gaps in the sub wire-strand portion are decreased by decreasing the flexibility of the sub wire strand, and thus, it is possible to suppress the occurrence of initial stretching. In other words, it is possible to form the first region so as to have a small diameter, and to suppress initial stretching of the main wire strand by means of the sub wire strand. By doing so, it is possible, even in medical equipment provided with a flexible inserted portion, to generate a desired driving force on a distal-end side thereof with a high responsiveness.

In the above-described aspect, a diameter of the sub wire-strand portion may be at most 1.5-times a diameter of the main wire-strand portion.

By doing so, it is possible to keep the outer diameter of the second region to be at most four-times that of the first region.

In addition, in the above-described aspect, the sub wire-strand portion may be formed of one sub wire strand and may satisfy the following conditional expression:

$$2a < \frac{\sin\frac{\pi}{n}}{1 - \sin\frac{\pi}{n}} \leq 1.5$$

where n is the number of the sub wire-strand portions, $d_c$ is the diameter of the main wire strand, $D_c$ is the diameter of the main wire-strand portion, and a is $d_c/D_c$.

In addition, in the above-described aspect, the number n of the sub wire-strand portions may be such that $5 \leq n \leq 17$.

By doing so, it is possible to achieve an effect of suppressing initial stretching in the case in which the main wire-strand portion is formed of at most 7×7 stranded wires.

In addition, in the above-described aspect, the sub wire-strand portion may be formed of one sub wire strand and the diameter of the sub wire strand may be at least four-times the diameter of the main wire strand.

By doing so, it is possible to set the product of the flexural rigidity and the lateral cross-sectional area for the sub wire-strand portion to be at least 100-times that for the main wire-strand portion, and thus, it is possible to determine the initial stretching on the basis of the sub wire-strand portion.

In addition, in the above-described aspect, the following conditional expression may be satisfied:

$$4a < \frac{\sin\frac{\pi}{n}}{1 - \sin\frac{\pi}{n}} \leq 1.5$$

where n is the number of the sub wire-strand portions, $d_c$ is the diameter of the main wire strand, $D_c$ is the diameter of the main wire-strand portion, and a is $d_c/D_c$.

In addition, in the above-described aspect, the number n of the sub wire-strand portions may be such that $5 \leq n \leq 10$.

In addition, in the above-described aspect, the sub wire strand may be formed of a material having a Young's modulus that is greater than that of the main wire strand.

By doing so, it is possible to increase the rigidity of the sub wire-strand portion, which greatly influences the initial stretching characteristics, relative to that of the main wire-strand portion, and thus, it is possible to decrease initial stretching.

In addition, another aspect of the present invention is medical equipment including: an elongated inserted portion possessing flexibility; a treating portion that is provided at a distal-end portion of the inserted portion and that includes an end effector; a manipulating portion that is provided on a base-end side of the inserted portion and that serves for manipulating the treating portion; and a medical wire according to any one of Claims 1 to 8, wherein the first region is connected to the treating portion, and the second region is connected to the manipulating portion.

In the above-described aspect, the following conditional expression may be satisfied:

$$d_a/d_c < d_j/d_m$$

where $d_a$ is the minimum bending radius of the first region in the treating portion, $d_j$ is the minimum bending radius of the second region in the manipulating portion, $d_c$ is the diameter of the main wire strand, and $d_m$ is the diameter of the sub wire strand.

By doing so, the bending radius is set in accordance with the wire-strand diameter, and thus, it is possible to prevent breakage of the medical wire and changes in the characteristics thereof.

The present invention affords an advantage in that it is possible, even in medical equipment provided with a flexible inserted portion, to generate a desired driving force on the distal-end side thereof with high responsiveness.

REFERENCE SIGNS LIST 1 medical wire
2 first region
3 second region
10 main wire-strand portion
20 sub wire-strand portion
101 medical equipment
110 inserted portion
120 treating portion
123 end effector
130 manipulating portion

The invention claimed is:

1. A medical equipment comprising:
   an elongated inserted portion possessing flexibility;
   an end effector provided at a distal side of the elongated insertion portion;
   a manipulating portion provided on a proximal side of the elongated inserted portion, the manipulating portion being configured to manipulate the end effector; and
   a medical wire comprising:
      a first region coupled to the end effector via a first pulley, the first region formed by only a main wire-strand portion; and
      a second region coupled to the manipulating portion via a second pulley, the second region formed by both the main wire-strand portion and a sub wire-strand portion,
   wherein the main wire-strand portion is formed of a plurality of main wire strands and is configured to be extended over the entire length of the medical wire,
   the sub wire-strand portion is configured to be secured to the main wire-strand portion at an outer circumference of the main wire-strand portion to prevent longitudinal movement of the sub wire-strand portion relative to the main wire-strand portion, the sub wire-strand portion being formed of at least one sub wire strand, and a diameter of the at least one sub wire strand is at least twice a diameter of each of the plurality of main wire strands, and
   wherein a following conditional expression is satisfied:
   $d_a/d_c < d_j/d_m$,
   where
   $d_a$ is the minimum bending radius of the first region,
   $d_j$ is the minimum bending radius of the second region,
   $d_c$ is the diameter of each of the plurality of main wire strands, and
   $d_m$ is the diameter of the at least one sub wire strand.

2. The medical equipment according to claim 1, wherein a diameter of the sub wire-strand portion is at most 1.5-times a diameter of the main wire-strand portion.

3. The medical equipment according to claim 2, wherein the sub wire-strand portion is formed of one sub wire strand and satisfies the following conditional expression:

$$2a < \frac{\sin\frac{\pi}{n}}{1-\sin\frac{\pi}{n}} \leq 1.5$$

where
n is the number of the sub wire-strand portions,
$D_c$, is the diameter of the main wire-strand portion, and
a is $d_c/D_c$.

4. The medical equipment according to claim 3, wherein the number n of the sub wire-strand portions is such that $5 \leq n \leq 17$.

5. The medical equipment according to claim 2,
   wherein the sub wire-strand portion is formed of one sub wire strand, and
   the diameter of the sub wire strand is at least four-times the diameter of the main wire strand.

6. The medical equipment according to claim 5, wherein the following conditional expression is satisfied:

$$4a < \frac{\sin\frac{\pi}{n}}{1-\sin\frac{\pi}{n}} \leq 1.5$$

where
n is the number of the sub wire-strand portions,
$D_c$, is the diameter of the main wire-strand portion, and
a is $d_c/D_c$.

7. The medical equipment according to claim 5 or 6, wherein the number n of the sub wire-strand portions is such that $5 \leq n \leq 10$.

8. The medical equipment according to claim 1, wherein the at least one sub wire strand is formed of a first material having a Young's modulus that is greater than a Young's modulus of a second material forming the plurality of main wire strands.

* * * * *